though the column pressure for such separations can be as high as 1800 mm. Hg, it can also range from 1 to 1800 mm. Hg, or even at atmospheric pressure, i.e., 760 mm. Hg

United States Patent [19]
Watson

[11] 3,986,937
[45] Oct. 19, 1976

[54] POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[22] Filed: Dec. 9, 1974

[21] Appl. No.: 531,067

[52] U.S. Cl. .................................. 203/9; 260/669 A
[51] Int. Cl.² ...................... B01D 3/00; C07C 7/18; C07C 15/00
[58] Field of Search ................. 203/8, 9; 260/669 A

[56] References Cited
UNITED STATES PATENTS

| | | | |
|---|---|---|---|
| 2,410,042 | 10/1946 | Bond, Jr. .................... | 260/669 A |
| 2,900,421 | 8/1959 | Kharasch .................... | 203/9 |
| 3,527,822 | 9/1970 | Benson, Jr. ................. | 203/9 |
| 3,647,637 | 3/1972 | Rosenwald .................. | 203/9 |
| 3,763,015 | 10/1973 | Morimoto .................... | 203/9 |
| 3,816,265 | 6/1974 | Daniels ....................... | 203/9 |

Primary Examiner—Jack Sofer

[57] ABSTRACT

Disclosed is a process for the distillation of readily polymerizable vinyl aromatic compounds which comprises subjecting such compounds to distillation conditions in the presence of an effective amount of $N_2O_3$ as a polymerization inhibitor.

7 Claims, No Drawings

POLYMERIZATION INHIBITOR FOR VINYL AROMATIC COMPOUNDS

BACKGROUND OF THE INVENTION

The present invention relates to a process for the distillation of readily polymerizable vinyl aromatic compounds, and more especially, to a process for the vacuum distillation of styrene, substituted styrene, divinylbenzene and polyvinylbenzenes wherein the amount of said materials polymerized during distillation is reduced over an extended period of time, wherein the material accummulating in the bottom or reboiler area of the distillation apparatus is free of material contaminated with sulfur and wherein the rate of throughput for a given distillation apparatus can be increased over the rate at which such apparatus may be operated in accordance with conventional methods.

It is well known that vinyl aromatic compounds such as monomeric styrene, lower alkylated styrene, e.g., alpha-methyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatics under distillation conditions include 4-tert-butylcatechol (TBC) and hydroquinone. It is preferred, however, to purify vinyl aromatics by using vacuum distillation techniques, whereby these commonly employed inhibitors are rendered unsuitable in view of the fact that they are effective only in the presence of oxygen. The partial pressure of oxygen in a vacuum distillation column is accordingly too low for these conventional inhibitors to be effective. Sulfur is perhaps the polymerization inhibitor most commonly employed to inhibit polymerization of vinyl aromatic compounds during distillation, since sulfur does provide effective inhibition in the absence of oxygen. While sulfur provides a reasonably effective inhibitor, its use in distillation processes results in one very significant disadvantage, namely, there is formed in the reboiler bottoms of the distillation column a valueless waste material which is highly contaminated with sulfur. This waste material furthermore represents a significant pollution or waste removal problem.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-nitroso phenylhydroxylamine and p-nitroso-N,N-dimethylaniline are reasonably effective inhibitors for the distillation of styrene, although they are not particularly soluble in styrene monomer. On the other hand, N-nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas N,N-nitroso-methylaniline as disclosed in U.S. patent application Ser. No. 288,138, also assigned to the assignee of the present application, has been found to be an excellent polymerization inhibitor for styrene under vacuum distillation conditions. One of the most effective inhibitor systems known for divinylbenzene comprises a mixture of sulfur and N-nitroso phenylhydroxylamine.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude divinylbenzene (a mixture containing divinylbenzenes, diethylbenzenes and monovinylbenzenes) to obtain high purity divinylbenzenes, even when inhibited with sulfur and TBC, a divinylbenzene product is obtained which contains significant quantities of polymer which are difficult to separate from the product and are detrimental to the end use of such divinylbenzenes. Furthermore, the material which is removed from the bottom or reboiler area of the distillation apparatus is a highly polluting sulfur-containing waste material which must be disposed of.

Nitrogen oxides are known according to the prior art to be effective for inhibiting polymerization of certain unsaturated compounds, and accordingly, have been employed as polymerization inhibitors in certain types of applications. However, the use of the normally-gaseous nitrogen oxides is predominantly confined to static conditions, e.g., storage, since the use of a gaseous material is strongly suggested against under any conditions where the inhibitor could readily escape. Thus, the use of normally gaseous inhibitors such as the nitrogen oxides has found substantially no application in distillation or similar purification processes involving heat, and this is particularly true in the case of vacuum distillation for the obvious reasons.

Accordingly, there exists a strong need for a polymerization inhibitor which will effectively prevent the polymerization of vinyl aromatic compounds during vacuum distillation thereof.

SUMMARY OF THE INVENTION

It is therefore an object of the present invention to provide a new and improved process for the distillazation of readily polymerizable vinyl aromatic compounds.

A further object of the invention is to provide a new and improved process for the distillation of readily polymerizable vinyl aromatic compounds, which process results in higher recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is still a further object of the present invention to provide a new and improved process for the distillation of vinyl aromatic compounds which provides all of the foregoing-enumerated advantages in a vacuum distillation process.

In accomplishing the foregoing and other objects, there has been provided in accordance with the present invention a process for the distillation of a readily polymerizable vinyl aromatic compound comprising subjecting the vinyl aromatic compound to distillation conditions in the presence of an amount of $N_2O_3$ to inhibit polymerization of the vinyl aromatic compound under the distillation conditions.

In one aspect of the process according to the invention, the normally gaseous inhibitor is simply introduced into the distillation system by injection into the reboiler area of the distillation apparatus, or alternatively, by injection into the incoming stream of vinyl aromatic compound to be purified. It is one salient feature of the invention that the mode of introducing and metering the amount of polymerization inhibitor is considerably simplified due to the ease of metering a normally gaseous material and due to the simplicity of the equipment necessary therefor.

The amount of $N_2O_3$ necessary to inhibit polymerization of the vinyl aromatic compounds may vary over a broad range depending upon various factors of the distillation process e.g., temperature, amount of reflux, if any, pressure residence time, etc. Typically, however, it has been found that an amount of inhibitor between about 50 and about 1000 ppm is sufficient to substantially inhibit polymerization of vinyl aromatic compounds under normal distillation conditions (105° C.).

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Also, the rate of operation of a given distillation apparatus can be increased over and above the rate of operation for the same apparatus utilizing conventional methods, since lower vacuum levels and higher distillation temperatures are possible according to the present invention. Still further, the material accummulating in the bottom or reboiler area of the distillation apparatus can be reused, e.g., for its fuel value or for reprocessing, which is a distinct advantage over conventional methods utilizing sulfur as a polymerization inhibitor which produce a highly polluting waste material in the reboiler area. Furthermore, it has also been found that any polymeric material inadvertently formed during the process of the invention is of a low molecular weight character and therefore presents fewer problems in connection with fouling of the distillation apparatus. Finally, use of the inhibitor according to the invention has proven to be surprisingly advantageous in preventing polymer build-up over the entire extend of the distillation apparatus, i.e., in the upper portions of the columns, whereas this result is not achieved in accordance with prior art methods.

DETAILED DESCRIPTION OF PREFERRED EMBODIMENTS

The distillation process of the present invention employs $N_2O_3$ as a polymerization inhibitor during the distillation process carried out under reduced pressure, e.g., vacuum distillation, and one of the significant advantages of the invention is that the use of sulfur in the distillation system can be avoided.

The distillation technique of the process of the present invention is suitable for use in virtually any type of separation of a readily polymerizable vinyl aromatic compound from a mixture wherein the vinyl aromatic compound is subjected to temperatures above room temperature. Surprisingly, the process of the present invention has been found particularly useful in vacuum distillation techniques, the preferred method for separating unstable organic liquid mixtures. In its most useful application, the distillation process of the invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude divinylbenzene or crude styrene under vacuum distillation conditions.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 and about 1000 ppm have generally provided suitable results, depending primarily upon the temperature of the distillation mixture and the degree of inhibition desired.

During vacuum distillation of divinylbenzene-containing mixtures and styrene-containing mixtures, the temperature of the reboiler is preferably maintained from about 150° F. to about 250° F. by controlling reboiler pressure at from about 30 mm. to about 400 mm. of Hg. Under such conditions, in a distillation apparatus having a distillation zone containing from about 50 to about 100 distillation steps, inhibitor concentrations of from about 20 to about 3000 ppm are suitable, whereas concentrations of from about 50 to about 1000 ppm are preferred in the case of styrene distillation and concentrations in the range of from about 100 to about 2000 ppm are preferred for distillation of vinylbenzenes. Obviously, amount of inhibitor greater than those specified hereinabove may be employed, although the advantages of adding the additional inhibitor are not significant and are outweighed by the corresponding increase in cost.

In addition, within the foregoing general ranges specified for the inhibitor concentration, preferred ranges have been developed. Thus, $N_2O_3$ is preferably employed in an amount of from about 50 to 500 ppm in the distillation of styrene compounds and in an amount of from about 100 to 1000 ppm in the distillation of divinylbenzene at temperatures between about 150° and 300° F., preferably, between 200° and 300° F. for styrene and residence times between about 2 and 4 hours. Obviously, in the lower portions of the temperature and residence time ranges, smaller amounts of inhibitor are required.

The normally gaseous polymerization inhibitor of the present invention may be introduced into the distillation apparatus in any convenient manner which permits efficient distribution of the inhibitor throughout the apparatus. Typically and most advantageously, the required amount of gaseous inhibitor is simply injected into the reboiler area of the distillation column, although equivalent results may be obtained by injecting the inhibitor into the incoming hot stream of vinyl aromatic compound. The gaseous nature of the inhibitor according to the invention provides significant advantages in terms of the ease with which addition of the inhibitor may be accomplished. Thus, the apparatus necessary for including the inhibitor may be greatly simplified over that required to introduce conventional inhibitors, since simple injection valves and conventional metering systems may be readily adapted for this purpose. In this way, control of the amount of inhibitor added is particularly simplified.

Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. A means by which the maintenance of the necessary inhibitor concentration is carried out is of no particular importance as long as the concentration of inhibitor is kept above the minimum required level.

It has been found in accordance with the invention that the volitility of the inhibitor provides unexpected advantages in terms of the degree of inhibition of polymer achieved during the subject distillation process. The volitility of the inhibitor of the invention causes it to be more effectively distributed throughout the entire length of the distillation apparatus. As a result, polymerization is more effectively inhibited at points in the apparatus remote from the reboiler area than is the case with conventional distillation processes using liquid or solid inhibitors. The need for adding inhibitor at various points in the distillation column is therefore eliminated.

Another factor enabling the distillation apparatus to operate at an increased rate in accordance with the present invention as opposed to conventional prior art processes is the fact that the inhibitor of the present invention is a more efficient inhibitor than the conventional inhibitors, and will thus permit higher distillation temperatures and higher pressures. In this way, the rate of distillation can be increased without increasing the amount of polymerization which has been deemed to be acceptable in accordance with conventional distillation procedures.

When the process of the present invention is utilized, the bottoms material which accummulates during the distillation process can be drawn off and utilized for its heating value or for reprocessing. This represents another significant advantage in comparison to conventional processes for vacuum distillation of vinyl aromatic compounds which employ sulfur as the polymerization inhibitor, or sulfur in combination with other chemical polymerization inhibitors. In these conventional processes, a bottoms material is formed which is valueless for further use and constitutes a highly polluting waste material which must be disposed of and which, in this regard, also presents a problem of disposal.

Upon recovery of the distillation product obtained from the process of the present invention, it is found that a higher percentage of the pure readily polymerizable vinyl aromatic compound is recovered in an unpolymerized state. Furthermore, it has been noted that the polymeric products which are formed during the distillation process of the invention exhibit significantly lower molecular weight characteristics than polymeric products formed in accordance with conventional distillation techniques in the presence of the usual inhibitors. This result provides the advantage that there is less fouling in the apparatus and accordingly less chance of plugging. Moreover, the concentrated distillation residues are more easily handled and removed from the apparatus, as by pumping or the like.

In order to more fully describe the present invention, the following Examples are presented which are intended to be merely illustrative and not in any sense limitative of the invention.

EXAMPLE 1

Two 100 ml. three neck reaction flasks fitted with reflux condensers, thermometers and magnetic stirrers are placed in an ordinary thermostatic, stirred hot oil bath. 50 ml. of styrene are placed in each flask. A nitrogen blanket is maintained over the stirred liquid in the control sample, whereas a very slow capillary bubbling (about two bubbles per second) is employed to bubble $N_2O_3$ through the test flask.

Analysis for the presence of polymerized styrene is carried out by combining 1 ml. samples of styrene from each flask with 3 ml. of methanol and examining the resulting mixture for turbidity. The following results are obtained:

The oil bath is maintained at a temperature of 90° C. over a 1 hour period. After ½ hour at this temperature, samples are taken from each of the flasks, whereupon the control flask is found to contain polymerized material and the $N_2O_3$-containing flask is found to be free of polymerized material. Repetition of the test at the end of one hour at this bath temperature confirms the foregoing results.

The temperature of the bath is increased to 105° C. and is maintained there approximately 1 hour. Tests conducted each half-hour show the presence of no polymer in the $N_2O_3$-containing flask.

The temperature of the oil bath is then raised to 115° C. and is maintained at this temperature for 1 hour. Again, tests conducted each half-hour evidence the formation of no polymer in the $N_2O_3$-containing flask.

The temperature of the oil bath is then raised to 125° C. and is maintained at this temperature for a period of 1 hour. Once again, tests at each half-hour interval confirm that no polymer is yet formed in the flask inhibited with $N_2O_3$.

The temperature of the oil bath is then raised to 150° C. and refluxing is begun in order to raise the temperature of the styrene to about 139° C. Under these conditions, the test finally indicates the formation of polymer in the flask containing $N_2O_3$. A total amount of $N_2O_3$ utilized during this test procedure is somewhat less than about 0.2 grams (about 4000 ppm over the run) and even after maintaining the styrene at a temperature of approximately 140° C. under reflux conditions for a period of ½ hour, the end product is not at all viscous, which indicates that the polymer content remains extremely low.

EXAMPLE 2

The procedure of Example 1 is repeated utilizing various known inhibitors. The samples of styrene containing these inhibitors are maintained at approximately 105° C. for a period of 4¼ hours, after which the samples are analyzed for polymer content. The results of these tests are set forth in Table I.

TABLE I

| Sample | Inhibitor | Inhibitor Concentration (by wt.) | Polymer Content % Wt. |
|---|---|---|---|
| 1 | None-Control | 0 | 15.5 |
| 2 | Sulfur | 500 ppm. | 2.8 |
| 3 | Sulfur | 1250 ppm. | 1.1 |
| 4 | Diphenylamine | 500 ppm. | 17.1 |
| 5 | N-nitroso-N-methylaniline | 300 ppm. | 1.6 |
| 6 | p-nitroso-N,N-dimethylaniline | 300 ppm. | 2.7 |
| 7 | N-nitroso diphenylamine | 300 ppm. | 0.3 |
| 8 | N-nitroso diphenylamine | 200 ppm. | 0.4 |
| 9 | Ni-nitroso diphenylamine | 150 ppm. | 0.6 |
| 10 | Nitrosophenon-sodium salt | .05% | 16.2 |
| 11 | Nitrosophenyl hydroxylamine | .05% | 0.6 |
| 12 | $N_2O_3$ | 100 ppm. | 0.4 |
| 13 | $N_2O_3$ | 250 ppm. | 0.3 |

EXAMPLE 3

30 ml. of divinylbenzene (containing 81% meta-isomer, 11.2% para-isomer, 716% naphthenes and 0.2% meta-ethylvinylbenzene) is withdrawn from storage and sealed in a 50 ml. flask with a septum closure. The divinylbenzene exhibits a faint cloud on testing with methanol, which indicates that some polymer has been formed upon storage. The flask is with nitrogen to remove all oxygen, and then 250 ppm of $N_2O_3$ gas is injected into the flask. The flask is placed in an agitated control temperature oil bath at 105° C., after a period of 2 hours at 105° C. the divinylbenzene is shown to be opaque by the methanol test, but the solution does not coagulate. After 3 hours at 105° C. little change is noted in the condition of the divinylbenzene; however, after 5 hours at this temperature, the divinylbenzene finally coagulates upon being tested with methanol.

The test is discontinued and after being cooled to room temperature, the divinylbenzene is still only slightly viscous. Recovery of the polymeric residue shows a content of about 11% polymer. The residue obtained is resinous and appears to be a low molecular weight, soluble polymer, a result which is surprising for divinylbenzene.

EXAMPLE 4

The procedure of Example 2 is repeated except that 250 ppm of N-nitroso diphenylamine is employed in place of the $N_2O_3$. After ¾ of an hour at 105° C. it is observed that the flask is approximately half filled with insoluble polymer. Upon removal of the flask from the bath, polymerization still continues and explodes the flask in approximately 1 minute, leaving dry solid pieces of insoluble polymer. Essentially 100% polymerization is observed.

What is claimed is:

1. A process for the distillation of a readily polymerizable vinyl aromatic compound, which comprises subjecting such compound to distillation conditions in the presence of $N_2O_3$ as a polymerization inhibitor, said $N_2O_3$ inhibitor being present in an amount of from about 50 ppm to about 1000 ppm based upon the contents of the distillation system, whereby polymerization of the vinyl aromatic compound in the distillation system is substantially inhibited.

2. The process as defined by claim 1, wherein said distillation conditions are vacuum distillation conditions.

3. The process as defined by claim 1, wherein said polymerization inhibitor is continuously added to said vinyl aromatic compound.

4. The process as defined by claim 1, wherein said vinyl aromatic compound is styrene.

5. The process as defined by claim 1, wherein said vinyl aromatic compound is divinylbenzene.

6. The process as defined by claim 1, wherein said distillation conditions comprise a temperature of between about 150° F. and 300° F.

7. The process as defined by claim 6, wherein said temperature is between about 200° F. and 300° F.

* * * * *